United States Patent
Eagle et al.

(10) Patent No.: US 10,471,144 B2
(45) Date of Patent: *Nov. 12, 2019

(54) COMBINATION OF LOCAL ROSE BENGAL AND SYSTEMIC IMMUNOMODULATIVE THERAPIES FOR ENHANCED TREATMENT OF CANCER

(71) Applicants: Provectus Pharmatech, Inc., Knoxville, TN (US); Pfizer, Inc., New York, NY (US)

(72) Inventors: Craig J. Eagle, New York, NY (US); H. Craig Dees, Knoxville, TN (US); Eric A. Wachter, Oak Ridge, TN (US); Jamie Singer, Knoxville, TN (US)

(73) Assignees: Provectus Pharmatech, Inc., Knoxville, TN (US); Pfizer, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/804,357

(22) Filed: Nov. 6, 2017

(65) Prior Publication Data

US 2018/0055926 A1  Mar. 1, 2018

Related U.S. Application Data

(63) Continuation of application No. 14/748,634, filed on Jun. 24, 2015, now Pat. No. 9,808,524, which is a continuation of application No. 13/416,494, filed on Mar. 9, 2012, now Pat. No. 9,107,887.

(60) Provisional application No. 61/451,395, filed on Mar. 10, 2011.

(51) Int. Cl.
| | |
|---|---|
| *A61K 39/395* | (2006.01) |
| *C07K 16/30* | (2006.01) |
| *A61K 31/352* | (2006.01) |
| *A61K 31/365* | (2006.01) |
| *A61K 39/00* | (2006.01) |
| *A61K 47/02* | (2006.01) |
| *A61K 38/19* | (2006.01) |
| *A61K 38/20* | (2006.01) |
| *A61K 38/21* | (2006.01) |
| *A61K 39/245* | (2006.01) |
| *C12N 7/00* | (2006.01) |
| *A61K 45/06* | (2006.01) |
| *A61K 47/60* | (2017.01) |

(52) U.S. Cl.
CPC ........ *A61K 39/3955* (2013.01); *A61K 31/352* (2013.01); *A61K 31/365* (2013.01); *A61K 38/193* (2013.01); *A61K 38/20* (2013.01); *A61K 38/204* (2013.01); *A61K 38/2006* (2013.01); *A61K 38/2013* (2013.01); *A61K 38/21* (2013.01); *A61K 38/212* (2013.01); *A61K 38/217* (2013.01); *A61K 39/0005* (2013.01); *A61K 39/0011* (2013.01); *A61K 39/245* (2013.01); *A61K 39/39558* (2013.01); *A61K 45/06* (2013.01); *A61K 47/02* (2013.01); *A61K 47/60* (2017.08); *C07K 16/30* (2013.01); *C12N 7/00* (2013.01); *A61K 2039/505* (2013.01); *C12N 2710/16021* (2013.01); *C12N 2710/16034* (2013.01)

(58) Field of Classification Search
None
See application file for complete search history.

(56) References Cited

U.S. PATENT DOCUMENTS

| | | | |
|---|---|---|---|
| 5,725,855 A | 3/1998 | Ochoa et al. | |
| 6,689,757 B1 | 2/2004 | Craig | |
| 7,378,233 B2 | 5/2008 | Sidransky et al. | |
| 7,442,507 B2 | 10/2008 | Polsky et al. | |
| 7,648,695 B2 | 1/2010 | Dees et al. | |
| 9,107,887 B2 | 8/2015 | Eagle et al. | |
| 2002/0161035 A1 | 10/2002 | Dees et al. | |
| 2005/0019918 A1 | 1/2005 | Sumimoto et al. | |
| 2005/0277118 A1 | 12/2005 | Roth et al. | |
| 2006/0246476 A1 | 11/2006 | Polsky et al. | |
| 2007/0087350 A1 | 4/2007 | Kappel | |
| 2007/0287838 A1 | 12/2007 | Niculescu-Duvaz et al. | |
| 2008/0015191 A1 | 1/2008 | Springer et al. | |
| 2008/0118567 A1 | 5/2008 | Scott et al. | |
| 2009/0074787 A1 | 3/2009 | Gomez-Navarro et al. | |
| 2009/0099190 A1 | 4/2009 | Flynn et al. | |
| 2009/0117199 A1 | 5/2009 | Scott et al. | |
| 2009/0325945 A1 | 12/2009 | Niculescu-Duvaz et al. | |
| 2010/0189651 A1 | 7/2010 | Stagliano et al. | |
| 2010/0286142 A1 | 11/2010 | Ibrahim et al. | |
| 2010/0298320 A1 | 11/2010 | Springer et al. | |

(Continued)

FOREIGN PATENT DOCUMENTS

| | | |
|---|---|---|
| EP | 1 043 026 A2 | 10/2000 |
| EP | 2 036 990 A1 | 3/2009 |

(Continued)

OTHER PUBLICATIONS

Waitz et al.—Cancer Res., 72, 430-439, 2011. (Year: 2011).*

(Continued)

*Primary Examiner* — Elly-Gerald Stoica
(74) *Attorney, Agent, or Firm* — Husch Blackwell LLP

(57) ABSTRACT

A method for the treatment of cancer comprising administration of a therapeutically effective amount of an intralesional chemoablative pharmaceutical composition, or variant of said composition, in combination with a therapeutically effective amount of a systemic immunomodulatory anticancer agent. A further method for the treatment of cancer comprising administration of a therapeutically effective amount of an intralesional chemoablative pharmaceutical composition, or variant of said composition, in combination with a therapeutically effective amount of a systemic targeted anticancer agent. The present invention is further directed to pharmaceutical compositions for treatment of cancer. The intralesional chemoablative pharmaceutical composition can comprise an IL chemoablative agent comprising primarily a halogenated xanthene.

26 Claims, No Drawings

(56) References Cited

U.S. PATENT DOCUMENTS

| | | | |
|---|---|---|---|
| 2011/0071217 | A1 | 3/2011 | Singer et al. |
| 2012/0263677 | A1 | 10/2012 | Eagle et al. |
| 2015/0290165 | A1 | 10/2015 | Eagle et al. |
| 2015/0290309 | A1 | 10/2015 | Eagle et al. |
| 2015/0290318 | A1 | 10/2015 | Eagle et al. |

FOREIGN PATENT DOCUMENTS

| | | |
|---|---|---|
| EP | 2 710 137 | 12/2014 |
| WO | WO 2006/048749 A1 | 5/2006 |
| WO | WO 2007/067959 A2 | 6/2007 |
| WO | WO 2007/113648 A1 | 10/2007 |
| WO | WO 2010/014784 A2 | 2/2010 |
| WO | WO 2010/081173 A2 | 7/2010 |
| WO | WO 2011/011027 A1 | 1/2011 |
| WO | WO 2012/122444 A1 | 9/2012 |

OTHER PUBLICATIONS

Chen et al.—Anti-CTLA-4 therapy results in higher CD4+ ICOShi T cell frequency and IFN-y levels in both nonmalignant and malignant prostate tissues PNAS, 106, 2729-2734, 2009. (Year: 2009).*

Den Brok et al., In Situ Tumor Ablation Creates an Antigen Source for the Generation of Antitumor Immunity, Cancer Res. 64, 4024-4029, 2004. (Year: 2004).*

Written Opinion, re Application No. PCT/US2012/028412, dated Jun. 22, 2013.

International Preliminary Report on Patentability, re Application No. PCT/US2012/028412, dated Sep. 10, 2013.

Den Brok, M. et al, "In Situ Tumor Ablation Creates an Antigen Source for the Generation of Antitumor Immunity," Cancer Research, vol. 64, Jun. 1, 2004, pp. 4024-4029.

Thompson, J.F. et al, "Chemoablation of Metastatic Melanoma Using Intralesional Rose Bengal," Melanoma Research, vol. 18, No. 6, 2008, pp. 405-411.

Eggermont, A.M.M. et al, "Anti-CTLA-4 Antibody Adjuvant Therapy in Melanoma," Seminars in Oncology, vol. 37, No. 5, Oct. 2010, pp. 455-459.

Paradis, T.J. et al, "The Anti-Tumor Activity of Anti-CTLA-4 is Mediated Through its Induction of IFNγ," Cancer Immunol. Immunother., vol. 50, 2001, pp. 125-133.

Linsley, P.S. et al, "Human B7-1 (CD80) and B7-2 (CD86) Bind with Similar Avidities but Distinct Kinetics to CD28 and CTLA-4 Receptors,"Immunity, vol. 1, No. 9, Dec. 1994, pp. 793-801.

Wachter, E. et al, "Abstract No. 4755" from the American Association for Cancer Research annual meeting, Washington, D.C., Apr. 6-10, 2013.

Dees, C. et al, "Poster Abstract No. 1452582," from the SITC Meeting Oct. 26-28, 2012.

Van Elsas, A. et al, "Combination Immunotherapy of B16 Melanoma Using Anti-Cytotoxic T Lymphocyte-associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation," J. Exp. Med., vol. 190, No. 3, Aug. 2, 1999, pp. 355-366.

Waitz, R. et al, "Potent Induction of Tumor Immunity by Combining Tumor Cryoablation with Anti-CTLA-4 Therapy," Cancer Research, vol. 72, No. 2, Jan. 15, 2012, pp. 430-439.

Demaria, S. et al, "Immune-Mediated Inhibition of Metastases after Treatment with Local Radiation and CTLA-4 Blockade in a Mouse Model of Breast Cancer," vol. 11, Jan. 15, 2005, pp. 728-734.

Toomey, P. et al, "Intralesional Injection of Rose Bengal Induces a Systemic Tumor-Specific Immune Response in Murine Models of Melanoma and Breast Cancer," PLOS ONE, vol. 8, No. 7, e68561, Jul. 2013, pp. 1-6.

Pilon-Thomas, S. et al, "Efficacy of Intralesional Injection with PV-10 in Combination with Co-Inhibitory Blockade in a Murine Model of Melanoma," presented at the Society for the Immunotherapy of Cancer meeting, National Harbor, MD, Nov. 6-9, 2014.

Del Rio, M.-L. et al, "Antibody-Mediated Signaling Through PD-1 Costimulates T Cells and Enhances CD28-dependent Proliferation," Eur. J. Immunol., vol. 35, 3545-3560.

Hodi, F.S. et al, "Improved Survival with Ipilimumab in Patients with Metastatic Melanoma," New England Journal of Medicine, vol. 363, No. 8, Aug. 19, 2010, pp. 711-723.

Chapman, P.B. et al, "Improved Survival with Vemurafenib in Melanoma with BRAF V600E Mutation," New England Journal of Medicine, vol. 364, No. 26, Jun. 30, 2011, pp. 2507-2516 (with supplementary appendix, 8 pages).

Dees, C. et al, "Generation of an Antitumor Response and Immunity Using a Small Molecule Drug (PV-10)," Society for Immunotherapy of Cancer (SITC) Annual Meeting, Oct. 26-28, 2012, abstract No. 1452582.

Ribas, A. et al, "Hepatotoxicity with Combination of Vemurafenib and Ipilimumab," New England Journal of Medicine, vol. 368, No. 14, Apr. 4, 2013, pp. 1365-1366. (doi: 10.1056/NEJMc1302338).

Andtbacka, R.H.I. et al, "OPTiM: A Randomized Phase 3 Trial of Talimogene Laherparepvec (T-VEC) vs. Subcutaneous Granulocyte-Macrophage Colony-Stimulating Factor (GM-CSF) for the Treatment of Unresected Stage 111B/C and IV Melanoma," presented at the American Society of Clinical Oncology (ASCO) Annual Meeting—Chicago, Jun. 2013.

Benson, Jr., D.M. et al, "The PD-1/PD-L1 Axis Modulates the Natural Killer Cell Versus Multiple Myeloma Effect: A Therapeutic Target for CT-011, A Novel Monoclonal Anti-PD-1 Antibody," Blood, vol. 116, No. 13, Sep. 30, 2010, pp. 2286-2294.

Iwai, Y. et al, "Involvement of PD-1 on Tumor Cells in the Escape from Host Immune System and Tumor Immunotherapy by PD-L1 Blockade," PNAS, vol. 99, No. 19, Sep. 17, 2002, pp. 12293-12297.

Kim, Y-S. et al, "Cancer Treatment Using an Optically Inert Rose Bengal Derivative Combined with Pulsed Focused Ultrasound," J Control Release, vol. 156, No. 3, pp. 315-322, Dec. 20, 2011.

Thompson, J.F et al, "Combination of Metastatic Melanoma Using Intralesional Rose Bengal," Melanoma Research, vol. 18, Jul. 30, 2008, pp. 405-411.

Examination Search Report re Canadian Patent Application No. 2,828,940, dated Nov. 15, 2016.

Onishi, H. et al, "New Immunotherapy Against Cancer: A Therapy to Control Regulatory T Cell," Fukuoka Medical Journal, vol. 101, No. 10, 2010, pp. 207-214.

O'Gorman, W.E. et al, "The Initial Phase of an Immune Response Functions to Activate Regulatory T Cells," The Journal of Immunology, vol. 183, No. 1, 2009, pp. 332-339.

Agarwala, S.S. et al, "Chemoblation of Metastatic Melanoma with Rose Bengal (PV-10)," Journal of Clinical Oncology, 2010 ASCO Annual Meeting Abstracts, vol. 28, No. 15, supplement 8534 (May 20 Supplement).

Agarwala, S.S. et al, "Chemoblation of Melanoma with Intralesional Rose Bengal (PV-10)," Journal of Clinical Oncology, 2009 ASCO Annual Meeting Proceedings (Post-Meeting Edition), vol. 27, No. 15 supplement 9060 (May 20 Supplement).

Foote, M.C. et al, "A Novel Treatment for Metastatic Melanoma with Intralesional Rose Bengal and Radiotherapy: A Case Series," Melanoma Research, 2010, vol. 20, No. 1, pp. 48-51.

Mori, T. "Ipilimumab, a New Molecular Targeted Therapy of Malignant Neoplastic Disease," Japan Journal of Cancer Chemotherapy, Jan. 2011, vol. 38, No. 1, pp. 31-35.

"Pigment Cell & Melanoma Research," Melanoma 2010 Congress, Dec. 2010, vol. 23, Issue 6, p. 874-1004.

News Release: "Provectus Announces Completion of PV-10 Phase 1 Trial in Patients with Liver Cancer," News Medical, Internet, URL:http://www.news-medical.net/news/20110127/Provectus-announces-completion-of-PV-10-Phase-1-trial-in-patients-with-liver-cancer.aspx, Jan. 27, 2011.

Li, J. et al, "Research and Development of Next Generation of Antibody-Based Therapeutics," Acta Phamacologica Sinica, 2010, vol. 31, pp. 1198-1207.

(56) References Cited

OTHER PUBLICATIONS

Brahmer, J.R. et al, "Phase I Study of Single-Agent Anti-Programmed Death-1(MDX-1106) in Refractory Solid Tumors: Safety, Clinical Activity, Pharmacodynamics, and Immunologic Correlates," Journal of Clinical Oncology, Jul. 1, 2010, vol. 28, No. 19, pp. 3167-3175.
Callahan, M.K. et al, "Anti-CTLA-4 Antibody Therapy: Immune Monitoring During Clinical Development of a Novel Immunotherapy," Semin Oncol, Oct. 2010, vol. 37, No. 5, pp. 473-484.
Berger, R. et al, "Phase I Safety and Pharmacokinetic Study of CT-011, a Humanized Antibody Interacting with PD-1, in Patients with Advanced Hematologic Malignancies," Clin Cancer Res, May 15, 2008, vol. 14, No. 10, pp. 3044-3051.
Sundar, R. et al, "Nivolumab in NSCLC: Latest Evidence and Clinical Potential," Therapeutic Advances in Medical Oncology, 2015, vol. 7, No. 2, pp. 85-96.
"Zinbryta" package insert.
"Synagis" package insert.
"Campath" package insert.
"Herceptin" package insert.
"Humira" package insert.
"Xolair" package insert.
"Avastin" package insert.
"Vectibix" package insert.
"Cimzia" package insert.
"Tecentriq" package insert.
"Vervoy" package insert.
"Keytruda" package insert.
"Opdivo" package insert.
Cao et al., *Lab Invest* 2011, 91:598-608.
Wachter Declaration in U.S. Appl. No. 13/416,494, Executed Dec. 5, 2014.
*Fundamental Immunology*, Third Edition, Paul ed., Raven Press, New York, (1993), p. 1320.
Garbe et al., *The Oncologist* 16:5-24 (2011).
Goldfarb et. al., *Intralesional Rose Bengal as an Oncolytic Immunotherapy for Hepatic Tumors*, Presentation No. PP0530, The 26$^{th}$ Conference for the Asian Pacific Association for the Study of the Liver, presented Feb. 16-19, 2017.
Goldfarb et al., Percutaneous Rose Bengal as an Oncolytic Immunotherapy for Hepatic Metastases, Abstract No. 15831, CIO 2017, Feb. 4-5, 2017.
Marabelle et al., *J. Clin. Invest.* 2013;123(6):2447-2463.
Citations to Marabelle et al., *J. Clin. Invest.* 2013;123(6):2447-2463.
William Broad and Nicholas Wade, *Betrayers of the Faith*, Simon and Schuster, New York (1982), p. 54.
Cole et al., *Science* 1972; 178:368-375.
Wachter Declaration and Exhibits filed in U.S. Pat. No. 9,107,887.
Chen et al.—Anti-CTLA-4 therapy results in higher CD4+ ICOS hi T cell frequency and IFN-.gamma. levels in both nonmalignant prostate tissues PNAS, 106, 2729-2734, 2009.
Provectus Announces completion of PV-10 Phase 1 trial in patients with liver cancer, News Jan. 27, 2011 Medical, Internet, URL:http://www.news-medical.net/news/20110127/Provectus-announces-complet- ion-of-PV-10-Phase-1-trial-in-patients-with-liver-cancer.aspx, Jan. 27, 2011.
Qin et al., "Colon Cancer Cell Treatment with Rose Bengal Generates a Protective Immune Response Via Immunogenic Cell Death", Cell Death and Disease (2017) 8, e2584; doi: 10.1038/cddis.2016.473, pp. 1-9 (www.nature.com/cddis).
Liu et al., "Intralesional Rose Bengal in Melanoma Elicits Tumor Immunity via Activation of Dentritic Cells by the Release of High Mobility Group Box 1", Oncotarget, vol. 7, No. 25, pp. 37893-37905, (2017).
Chen et al., "Oncology Meets Immunology: The Cancer-Immunity Cycle", Cell Press, Immunity 39, Jul. 25, 2013, Elsevier Inc., pp. 1-10.
Written re Application No. PCT/US2012/028412, dated Jun. 22, 2012.
International Search Report re Application No. PCT/US2012/028412, dated Jun. 22, 2012.
Extended European Search Report re Application No. Ep 12755115.8, dated Dec. 3, 2014.
Pilon-Thomas et al, 2016 [American Association for Cancer Research (AACR) Annual Meeting, Apr. 16-20, 2016, Abstract No. 4978].
Patel et al, Poster at 2018 SMR Conference of the Society for Melanoma Research, Manchester, England, Oct. 24-27, 2018.
Agarwala et al, Poster at 2018 SMR Conference of the Society for Melanoma Research, Manchester, England, Oct. 24-28, 2018.
Agarwala et al, Poster at Melanoma Bridge 2018, Napoli, Nov. 29-Dec. 1, 2018.
Swift et al, Poster at American Society of Clinical Oncology (ASCO) Annual Meeting, Jun. 2, 2018.
Swift et al, *Onco Targets Ther* 12:1293-1307 (2019).
Liu et al, *Plos One* 13(4):e0196033 (Apr. 25, 2018).
Swift et al, ASCO Jun. 2, 2018; Poster.
Price et al, 2018 (European Society of Medical Oncology ESMO 2018 annual, presented Oct. 21, 2018.
Maker et al, *J Clin Cell Immunol.* Aug. 2015 6(4):343.
Srinivasan et al, *Plos Med* 15(1):e31002497 (Jan. 29, 2018).
Thompson et al, *Ann Surg Oncol* 22:2135-2142 (2015).

\* cited by examiner

COMBINATION OF LOCAL ROSE BENGAL AND SYSTEMIC IMMUNOMODULATIVE THERAPIES FOR ENHANCED TREATMENT OF CANCER

This application is a continuation of copending U.S. application Ser. No. 14/748,634 filed on Jun. 24, 2015 which is a continuation of U.S. application Ser. No. 13/416,494 filed on Mar. 9, 2012 (now U.S. Pat. No. 9,107,887 issued Aug. 18, 2015) which claims the benefit of U.S. provisional application 61/451,395 filed Mar. 10, 2011.

FIELD OF THE INVENTION

This invention relates to the fields of oncology and improved therapeutic regimens therefore.

BACKGROUND OF THE INVENTION

Pharmacologic approaches for treating cancer have traditionally relied on the use of various single agent systemic therapies (monotherapies). An archetypical example is chemotherapy, which utilizes broadly cytotoxic drugs that target rapidly dividing cells, including alkylating agents like dacarbazine (DTIC) or temozolomide (TMZ), or mitotic inhibitors like paclitaxel, to inhibit or kill the rapidly growing cells typical of cancer. Tumors may not be completely responsive to such monotherapy, either due to their high collateral systemic toxicity necessitating lower, even sub-therapeutic doses or development of tumor resistance that circumvents the activity of the monotherapy agent. More advanced chemotherapy strategies have been developed that are predicated on use of multiple agents in a combination therapy that simultaneously attack the tumor along multiple of biochemical pathways. Many of these regimens, such as the combination of doxorubicin, bleomycin, viblastine and DTIC for Hodgkin's lymphoma, have been developed through empirical testing. Because of the inherent limitations of their individual pharmacologic components, such approaches remain relatively non-specific with high morbidity, allowing considerable room for improvement in terms of efficacy and safety.

Targeting cancers based on their selective overexpression of certain cell-surface receptors or reliance on specific signaling or metabolic pathways, in particular aberrant pathways present in certain cancers, provides another point of attack. For instance, it has been found that some cancers harbor mutations in certain protein kinases, such as those encoded by the serine/threonine-protein kinase B-Raf gene (BRAF), that are involved in cell signaling and hyperproliferative growth, thereby serving an oncogene role. Targeting these pathways through the use of inhibitors has proven attractive, at least initially, in controlling cancers by staving off the oncolytic signaling. A similar approach based on targeting overexpression of certain receptors, such as epidermal growth factor receptor (EGFR) or vascular endothelial growth factor (VEGF), provides the basis for damping the oncolytic activity of these receptors, for instance by use of antibodies to the targeted receptors (or by use of agents that inhibit the signaling stimulated by these receptors). Unfortunately, as in the case of conventional chemotherapy, these receptors and pathways may play important physiologic roles peripheral to the tumor, leading to toxicity upon their targeting, while the targeted cells also may develop resistance by harnessing alternate biochemical processes or proliferating via selection of resistant clonal subpopulations of tumor cells. Thus, the challenges posed by these types of targeted therapies are substantially similar to those posed by conventional chemotherapy.

In a growing number of oncology indications it is now clear that cancerous tumors employ various methods to evade detection as aberrant tissue and to reduce immune system competency, thereby avoiding potential identification and destruction by the patient's immune system. As a consequence, a number of approaches have been developed to enhance the capability of the patient's immune system to detect and destroy cancers. For example, the anti-CTLA-4 (cytotoxic T lymphocyte-associated antigen 4) antibodies ipilimumab and tremelimumab are designed to counter downregulation of the immune system by blocking CTLA-4 activity and thus augmenting T-cell response against cancer. Alternate approaches may utilize agents that stimulate certain components of the immune system (i.e., upregulation), including administering non-specific cytokines (such as interleukin 1, 2, or 6, "IL-1", "IL-2" or "IL-6"; interferon-alpha or gamma, "IFN-α" and "IFN-γ"; and granulocyte macrophage colony stimulating factor, "GM-CSF"), or that attempt to provoke a tumor-specific immune response to certain tumor antigens, such as dendritic cell vaccines and antibodies against specific tumor antigens and even adoptive T-cell therapy. Additional approaches have attempted to elicit systemic response following repeated inoculation of tumors with certain immunostimulatory agents, such as an intralesional vaccine containing an oncolytic herpes virus encoding GM-CSF or a plasmid encoding human leukocyte antigen-B7 and beta-2 microglobulin agent designed to express allogeneic major histocompatibility complex (MHC) class I antigens. For various reasons including, but not limited to, potential systemic toxicity of these immunomodulating agents, differential expression of the targeted moieties or responsiveness of clonal subpopulations, increase of tumor burden during therapy induction, and development of resistance against the selected mode of attack, current regimens may not result in as robust an immune response as desired, again allowing considerable room for improvement in terms of efficacy and safety.

Combination of systemic immunomodulatory agents with systemic chemotherapy agents or kinase inhibitors has been proposed, for example by Jure-Kunkel and Lee (WO 2010/014784), however there is limited data to determine whether such an approach will be clinically significant. In principal, this approach combines the features of targeted therapy (using chemotherapy or a metabolic inhibitor) with immunomodulation in a combination therapy, and as is the case with standard chemotherapeutic combination therapy it provides a means to attack cancer simultaneously via several different paths, thereby increasing potency while reducing likelihood of resistance. Since the immunologic consequences of chemotherapy may at least partially counteract the activity of the immunomodulator, and their respective systemic adverse effects may be additive or synergistic, such a combination of modalities has significant potential shortcomings. While not the topic of Jure-Kunkel and Lee, targeted therapies when combined with immunomodulatory agents can also have these negative effects. Perhaps most importantly, these potential combinations don't appear to afford additive or synergistic tumoricidal potency in terms of immunologic benefit since neither chemotherapy nor metabolic or aberrant gene targeting can be expected to significantly activate an antitumor immune response, while the proposed anti-CTLA-4 targeting is similarly unlikely to increase sensitivity of tumor cells to the companion chemotherapy or tumor specific approach. The possibility of increased tumor burden during induction of immunomodulatory therapy further complicates the picture, raising the possibility that the disease may progress to an unacceptably advanced state during the early phases of the regimen.

Further complicating the therapeutic challenge, tumors that shrink gradually over a long period of time and slowly release immunoreactive tumor materials in response to any of these conventional systemic therapies may fail to trigger a potent protective response and can instead facilitate reduced antitumor immunity. This phenomenon is similar to that underlying low dose therapies for allergies whereby the host is repeatedly exposed to low doses of antigenic material over a prolonged period, eliciting tolerance by causing the immune system to identify these persistent "background" antigens as "self" (i.e., a normal part of the host). In a similar fashion, the slow, low dose release of tumor antigens to the immune system in response to many systemic therapies may deceive the immune system into tolerance toward tumor antigens thereby reducing or negating possible antitumor response, potentially prolonging tumor survival, and allowing continued metastatic spread.

An alternate class of therapies is predicated on physical restriction of delivery of the therapeutic modality to diseased tissue. These localized therapies attempt to maximize potency of the therapy within tumor tissue while reducing systemic exposure. Approaches include physical or chemical disruption of tumors using intralesional methods, such as percutaneous ethanol injection therapy (PEIT) and radiofrequency (RF) ablation, and locoregional delivery of potent cytotoxic agents, such as isolated limb perfusion (ILP), isolated limb infusion (ILI) or percutaneous hepatic perfusion (PHP), with melphalan (an alkylating agent) or similar agents. While these approaches are often quite effective in maximizing pharmacologic activity against the treated tumor, they have generally exhibited many of the same limitations of systemic therapies due to the inherent shortcomings of the underlying therapeutic modality, including limited specificity for the targeted cancer with significant locoregional toxicity, and minimal impact on systemic disease, particularly for those approaches having no mechanism for immune stimulation against the treated tumor.

The use of cancer-specific cytotoxic agents delivered via an intralesional (IL) route (i.e., IL chemoablation) is a novel hybrid approach that has been described by one or more of the present inventors (for example in U.S. Pat. No. 7,648,695, U.S. Ser. No. 11/951,800 and U.S. Ser. No. 12/315,781, which are incorporated herein in their entirety). This approach maximizes local efficacy against injected tumors while minimizing systemic exposure of the patient to the injected agent and resultant potential for systemic adverse effects. One or more of the present inventors have shown that IL use of a certain specific class of agent (for example certain formulations of certain halogenated xanthenes, exemplified by a 10% (w/v) solution of rose bengal disodium in saline, termed "PV-10" and undergoing clinical testing for treatment of metastatic melanoma, breast carcinoma and hepatocellular carcinoma) can elicit not only highly specific ablation of the injected lesion but also an antitumor immune response ("bystander effect") that can augment local efficacy in the injected tumor and lead to spontaneous regression of uninjected tumors. Nonclinical evidence indicates that high levels of granulocytes (such as basophils, eosinophils and mast cells) may be expressed in the tissue surrounding tumors, indicating that the host is attempting to mount a non-specific immune response to tumor tissue. Treatment of tumors with PV-10 can lead to modulation of this response to one that is more specific and effective (for example, by recruiting mononuclear tumor-infiltrating lymphocytes, TILs, or macrophages into and around the tumor). It is likely that acute tumor disruption resulting from IL chemoablation with PV-10 releases sequestered, intact tumor antigens to local antigen-presenting cells (APCs), facilitating modulation of the immune response and presentation of appropriate antigenic targets to T and B-cells. Collateral destruction of granulocytes surrounding the tumor may precipitate chemokine release and local inflammation, and may serve an adjuvant role in promoting specific antitumor response. In situ destruction of the injected tumor assures presentation of tumor antigens in their natural context, thereby maximizing potential response of the immune system to the treated tumor and to tumors bearing the same immunologic signature. Since immune response is proportional to the intensity and duration of the insult to the host, the acute exposure achieved through IL chemoablation is immunologically advantageous relative to the lesser intensity insult produced by a systemic therapy that is spread out over a long duration, and this acute exposure potentially vaccinates the patient against the treated tumor.

Acute ablation of the injected tumor also quickly reduces tumor burden, which may be augmented by injecting all or a substantial fraction of a patient's tumors, either in a single treatment session or a series of treatments fractionated over a period of days or weeks. This may reduce the level of immune suppression exerted by the patient's tumor mass, leading to improved ability of their immune system to mount a successful attack against remaining tumor tissue. The inherent suitability of IL chemoablation for use against large or multiple cancerous lesions, when present, may further enhance outcome by facilitating in situ inoculation against potentially distinct clonal subpopulations in different tumors (or even within individual tumors) that may arise during tumor growth and metastasis.

While IL chemoablation overcomes many of the shortcomings of prior therapeutic modalities (for example by achieving rapid reduction in tumor burden, maximizing acute exposure to intact tumor antigens in an appropriate context, and affording minimal potential for systemic adverse effects) one or more of the present inventors have found that it may not be ideal for all cancer cases, particularly certain advanced cases having rapidly proliferating tumors, those with widely disseminated disease and those that present in forms that are difficult to fully infiltrate with the IL agent. Accordingly, additional advancements are needed in the fields of oncology and improved therapeutic regimens therefore.

SUMMARY OF THE INVENTION

The present invention is directed to a method for the treatment of cancer, said method comprising administration of a therapeutically effective amount of an intralesional chemoablative pharmaceutical composition, or variant of said composition, in combination with a therapeutically effective amount of a systemic immunomodulatory anticancer agent.

The present invention is also directed to a pharmaceutical composition for the treatment of cancer comprising: a therapeutically effective amount of an intralesional chemoablative pharmaceutical composition; and a therapeutically effective amount of a systemic immunomodulatory anticancer agent.

In an embodiment of the above method and pharmaceutical composition, the systemic immunomodulatory anticancer agent comprises anti-CTLA-4 antibodies including ipilimumab and tremelimumab.

In an embodiment of the above method and pharmaceutical composition, the systemic immunomodulatory anticancer agent is selected from the group consisting of non-specific cytokines, such as interleukin-1, interleukin-2, or interleukin-6 (IL-1, IL-2 or IL-6) and aldesleukin; interferon-alpha or interferon-gamma (IFN-α and IFN-γ), interferon alfa-2b and pegylated interferon (including pegylated interferon alfa-2a and pegylated interferon alfa-2b); granulocyte macrophage colony stimulating factor (GM-CSF, molgramostim or sargramostim); dendritic cell vaccines and other allogeneic or autologous therapeutic cancer vaccines, including intralesional vaccines containing an oncolytic herpes virus encoding GM-CSF (OncoVex®) or a plasmid encoding human leukocyte antigen-B7 and beta-2 microglobulin agent designed to express allogeneic MHC class I antigens (Allovectin-7®); and antibodies against specific tumor antigens.

The present invention is also directed to a method for the treatment of cancer, said method comprising administration of a therapeutically effective amount of an intralesional chemoablative pharmaceutical composition, or variant of said composition, in combination with a therapeutically effective amount of a systemic targeted anticancer agent.

The present invention is also directed to a pharmaceutical composition for the treatment of cancer comprising: a therapeutically effective amount of an intralesional chemoablative pharmaceutical composition; and a therapeutically effective amount of a systemic targeted anticancer agent.

In an embodiment of the above method and pharmaceutical composition, the systemic targeted anticancer agent is selected from the group consisting of drugs that target protein kinases and the receptors that activate them, including afatinib (BIBW 2992), bevacizumab, cetuximab, dasatinib, E7080, erlotinib, gefitinib, imatinib, lapatinib, nilotinib, panitumumab, pazopanib, pegaptanib, ranibizumab, sorafenib, sunitinib, trastuzumab and vandetanib; serine/threonine-selective protein kinase inhibitors, including those targeting the B-Raf/MEK/ERK pathway, such as vemurafenib (also known as PLX4032, RG7204 or RO5185426), GSK2118436 and GSK1120212; aromatase inhibitors, including aminoglutethimide, anastrozole, exemestane, fadrozole, formestane, letrozole, testolactone and vorozole; estrogen receptor antagonists, including lasofoxifene, raloxifene, tamoxifen and toremifene; COX-2 inhibitors, including celecoxib, valdecoxib and rofecoxib; angiogenesis blockers, including IFN-α, IL-12, suramin, and thrombospondin (including thrombospondin 1, ABT-510 and ABT-898); and immune cell therapy, including adoptive T-cell transfer and autologous immune cell therapy.

In a further embodiment of all of the above methods and pharmaceutical compositions, the intralesional chemoablative pharmaceutical composition comprises an IL chemoablative agent comprising primarily a halogenated xanthene in an appropriate pharmaceutical composition, including a 0.1% (w/v) or higher concentration aqueous solution of the halogenated xanthene or mixtures thereof, or a physiologically acceptable salt of the halogenated xanthene.

In a further embodiment of all of the above methods and pharmaceutical compositions, the halogenated xanthene is rose bengal (4,5,6,7-tetrachloro-2',4',5',7'-tetraiodofluorescein).

In a further embodiment of all of the above methods and pharmaceutical compositions, the halogenated xanthene is rose bengal disodium.

In a further embodiment of all of the above methods and pharmaceutical compositions, the halogenated xanthene is selected from the group consisting of erythrosin B, phloxine B, 4,5,6,7-tetrabromo-2',4',5',7'-tetraiodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein.

In a further embodiment of all of the above methods and pharmaceutical compositions, the halogenated xanthene has a concentration of about 0.1% (w/v) up to about 20% (w/v), and that the pharmaceutical composition includes an electrolyte comprising at least one cation selected from the group consisting of sodium, potassium, calcium and magnesium and at least one anion selected from the group consisting of chloride, phosphate and nitrate, wherein the electrolyte is at a concentration of between about 0.1% (w/v) and about 2% (w/v).

In a further embodiment of all of the above methods and pharmaceutical compositions, the concentration of said electrolyte in the IL chemoablative pharmaceutical composition is between 0.5 to 1.5% (w/v).

In a further embodiment of all of the above methods and pharmaceutical compositions, the chemoablative pharmaceutical composition has an osmolality of the composition of greater than about 100 mOsm/kg.

In a further embodiment of all of the above methods and pharmaceutical compositions, the electrolyte is sodium chloride.

In a further embodiment of all of the above methods and pharmaceutical compositions, the pharmaceutical composition comprises a hydrophilic vehicle.

In a further embodiment of all of the above methods and pharmaceutical compositions, the pharmaceutical composition has a pH in the range of between about 4 to about 10.

In a further embodiment of all of the above methods and pharmaceutical compositions, the pharmaceutical composition has a pH in the range of between about 5 to about 7.

In a further embodiment of all of the above methods and pharmaceutical compositions, the methods and pharmaceutical compositions are for the treatment of cancers selected from melanoma, breast cancer, primary and metastatic liver cancer, prostate cancer and small cell and non small cell lung cancer.

DETAILED DESCRIPTION OF THE PRESENTLY PREFERRED EMBODIMENTS

One aspect of the present invention is the result of unanticipated synergy resulting upon combination of certain local therapeutic modalities, and in particular certain local immunomodulative therapies such as for example IL chemoablation with PV-10 or another halogenated xanthene agent, with certain systemic therapeutic modalities. This combination can boost the therapeutic activity of both therapeutic modalities with the potential for no significant increase, or even an overall decrease, in morbidity relative to that typically achieved using the component therapies separately.

One or more of the present inventors have shown that IL chemoablation can lead to rapid reduction in a patient's tumor burden, reducing potential for tumor-induced immune suppression, extent and severity of the disease, and continued drag on the patient's immune and other physiologic functions. The resultant acute exposure of the patient's immune system to intact tumor antigens in proper biological context is markedly different from that achieved using systemic chemotherapy, targeted systemic therapies, or other local therapeutic modalities, each of which generally produce at best a gradual, low level chronic exposure of the immune system to tumor antigens, often in an inappropriate context. Chemoablation of entire tumors or substantially the entirety of tumors, and especially chemoablation of multiple tumors, enhances exposure of the patient's immune system to any distinct clonal subpopulations of tumor cells that may be present, maximizing overall response to the in situ antitumor vaccination. Hence, the immunomodulatory effects achieved may be superior in breadth and potency to those achieved using prior therapeutic approaches.

However, for cases where disease is rapidly proliferating, or is widely disseminated, or presents in a form difficult to fully infiltrate with the IL chemoablative agent, use of complementary therapeutic modalities offers additive or synergistic benefit, particularly when they contribute immunologic stimulation (i.e., immunodulation) that complements that afforded through IL chemoablation. The use of such complementary immunomodulative therapies may have further advantage in terms of additive or synergistic immunologic interactions that allow one or both therapies to be used at reduced doses (relative to that needed when used individually as monotherapies) while retaining high efficacy, thereby reducing undesirable adverse effects.

In particular, the use of a potent local immunomodulative therapy, such as IL chemoablation with, for example, PV-10 or another halogenated xanthene agent, in conjunction with one or more systemic immunomodulative therapies (especially those that elicit immune system upregulation or counter tumor-induced immune system down regulation) is highly attractive since this combination yields a uniquely salubrious combination: exposure of the patient's potentiated immune system to the intense antigenic "insult" produced upon IL chemoablation. The effects of such combination may be heightened by potentiation of the immune system at the time of chemoablation or subsequent to chemoablation. Since IL chemoablation is well suited to repeat treatment, continued potentiation of the patient's immune system, for example by continued administration of the systemic immunomodulatory therapy, while IL chemoablation is administered one or more times, is a preferred embodiment. As an alternate embodiment, IL chemoablation may be followed by commencement of systemic immunomodulatory therapy, for example after a delay of several weeks or more when a reduction in local inflammation or other non-specific immunologic effects is desirable.

The potential of benefits of combining local immunomodulatory therapy with a systemic immunomodulatory therapy regimen may make otherwise undesirable systemic immunomodulatory therapies viable: due to the resultant augmentation in potency of the systemic component of the combination therapy, reduced systemic dose regimens may be possible with commensurate reduction in adverse effects from the systemic therapy. Further, since the adverse effect profile of the local immunomodulatory therapy (i.e., IL chemoablation) is orthogonal to that of most systemic immunomodulatory therapies, a combined local and systemic immunomodulatory therapy is inherently safer and more attractive compared with prior combinations that can produce undesirable additive or synergistic adverse effects.

The combination of massive exposure to tumor antigens coupled with reduced tumor burden that results from IL chemoablation is particularly attractive in this context, since it maximizes potential immune activation while diminishing potential immune downregulation and physiologic demand from the tumor mass. When combined with a systemic therapy that further enhances immunologic upregulation or reduces downregulation, the effects on antitumor immunity, both at the ablated lesion and at uninjected sites, including those proximal and distant to the injection sites, will be additive or synergistic.

Many of the advantages accrued upon combining local immunomodulatory therapy with a systemic immunomodulatory therapy may be achieved through similar combination of local immunomodulatory therapy with a systemic targeted therapy, such as IL chemoablation combined with a targeted kinase inhibitor. Since IL chemoablation has a uniquely disruptive effect on tumor tissue, combination of this modality with an approach that targets tumor viability via an orthogonal path, such as those that target aberrant growth signaling or overexpression of receptors involved in tumor hyperproliferation, can yield enhanced efficacy in the treated tumor. For example, by using a systemic targeted therapy to increase stress on the tumor or reduce tumor viability in the wake of IL chemoablation, the cytotoxicity of the IL treatment may be enhanced at the time of IL treatment; response of any remaining tumor tissue may also be increased to immunologic activation resulting from the IL treatment since the systemic therapy will counter proliferation of residual tumor tissue without interfering with development of the immune response from chemoablation. The rapid reduction in tumor burden resulting from IL chemoablation further augments these advantages by reducing immune suppression and physiologic demands from the tumor tissue. Since the systemic targeted therapy is not required to achieve complete control or eradication of substantial tumor masses in this context, but rather serves to augment the activity of the local immunomodulatory therapy, it may be possible to administer the systemic therapy at a reduced dose, thereby minimizing potential adverse effects and making the combined therapy safer and more attractive compared with prior systemic combinations. Addition of the immunologic response resulting from the local immunomodulatory therapy component provides a means to counter resistance problems that have plagued many targeted systemic therapies, such as the BRAF inhibitors, particularly when continuous systemic therapies are required to maintain long term control of the disease, since long term control will result from the immune response rather than perpetual reliance on the targeted systemic therapy.

In some cases it may be desirable to commence systemic targeted therapy prior to local immunomodulatory therapy, for instance when disease burden is very high or widespread, or when the disease is rapidly proliferating, potentially making effective administration of the local immunomodulatory therapy difficult or less effective. In this manner, the systemic targeted therapy may be used to control or reduce tumor burden prior to administration of local immunomodulatory therapy in order to enhance responsiveness of the disease to the local immunomodulatory therapy. Such an approach is tantamount to "down staging" disease status prior to commencement of local immunomodulatory therapy. For example, certain BRAF inhibiting drugs have proven effective at temporarily reducing disease burden in advanced stage metastatic melanoma, but resistance often develops within a period of months, negating long term outcome. Treatment of residual disease with local immunomodulatory therapy, such as IL chemotherapy, while it remains under control of the targeted therapy provides a means for elimination of residual tumor burden while stimulating long term immunity to recurrence, thereby improving ultimate outcome.

Problems affecting attempts to develop and utilize therapeutic cancer vaccines may also be similarly mitigated or resolved through combination of such vaccines with local immunomodulatory therapy. Specifically, lack of survival benefit observed in clinical trials of some such vaccines in advanced stage cancer, such as Canvaxin for stage III or IV melanoma, appears to be due in part to failure of vaccination to overcome existing tumor burden present in patients at the time of vaccination and continued increase in their disease level during the induction interval necessary for development of an immune response from vaccination. As in the case with systemic targeted therapy, the rapid reduction in tumor burden resulting from IL chemoablation can mitigate suppression of the immune system by the patient's disease burden while providing critical time for onset of the immune response from vaccination, thereby maximizing potential local and systemic antitumor effects through the combined action of the local immunomodulatory therapy and systemic vaccination.

Examples of combination therapies and method of treatment within the present invention include but are not limited to the following:

Local immunomodulative therapy combined with one or more systemic inhibitor of immune system down regulation, such as anti-CTLA-4 antibodies including but not limited to ipilimumab and tremelimumab.

Local immunomodulative therapy combined with one or more systemic immune upregulating agent, including: non-specific cytokines, such as interleukin-1, -2, or -6 (IL-1, IL-2 or IL-6) and aldesleukin; interferon-alpha or gamma (IFN-α and IFN-γ), interferon alfa-2b and pegylated interferon (including pegylated interferon alfa-2a and pegylated interferon alfa-2b); granulocyte macrophage colony stimulating factor (GM-CSF, molgramostim or sargramostim); dendritic cell vaccines and other allogeneic or autologous therapeutic cancer vaccines, including intralesional vaccines containing an oncolytic herpes virus encoding GM-CSF (OncoVexf) or a plasmid encoding human leukocyte antigen-B7 and beta-2 microglobulin agent designed to express allogeneic MHC class I antigens (Allovectin-7); and antibodies against specific tumor antigens.

Local immunomodulative therapy combined with one or more systemic targeted therapy agent, including: drugs that target protein kinases and the receptors that activate them, including but not limited to afatinib (BIBW 2992), bevacizumab, cetuximab, dasatinib, E7080, erlotinib, gefitinib, imatinib, lapatinib, nilotinib, panitumumab, pazopanib, pegaptanib, ranibizumab, sorafenib, sunitinib, trastuzumab and vandetanib; serine/threonine-selective protein kinase inhibitors, including but not limited to those targeting the B-Raf/MEK/ERK pathway, such as vemurafenib (also known as PLX4032, RG7204 or RO5185426), GSK2118436 and GSK1120212; aromatase inhibitors, including but not limited to aminoglutethimide, anastrozole, exemestane, fadrozole, formestane, letrozole, testolactone and vorozole; estrogen receptor antagonists, including but not limited to lasofoxifene, raloxifene, tamoxifen and toremifene; COX-2 inhibitors, including but not limited to celecoxib, valdecoxib and rofecoxib; angiogenesis blockers, including IFN-α, IL-12, suramin, and thrombospondin (including thrombospondin 1, ABT-510 and ABT-898); and immune cell therapy, including but not limited to adoptive T-cell transfer and autologous immune cell therapy.

Typically, monotherapy dose schedules are set by determining the maximum tolerated dose (MTD) in early-stage clinical trials. The MTD (or a close variation thereon) is then promulgated to later-stage clinical trials for assessment efficacy and more detailed assessment of safety. These MTDs frequently become the established therapeutic dose upon completion of clinical testing. Example dosing schedules for a number of systemic agents that may be combined in the present invention with local immunomodulative therapy are provided in Table 1.

TABLE 1

Example systemic immunomodulatory or targeted anticancer agents

| Systemic Agent | Typical Dose Schedule |
|---|---|
| Ipilimumab | 3 mg/kg q21d for 4 treatments |
| Tremelimumab | 15 mg/kg q3m |
| Aldesleukin | 600,000 IU/kg q8h (up to 14 doses before 9 day rest and repeat; rest at least 7 wks before repeat of course) |
| interferon alfa-2b | 20 million IU/m$^2$ 5 times per week for 4 weeks (induction phase) followed by 10 million IU/m$^2$ three times per week (maintenance phase) |
| pegylated interferon | 6 µg/kg qwk for eight weeks (induction phase) followed by 3 µg/kg qwk (maintenance phase) |
| Oncovex ® | 4 mL IL at 10$^8$ pfu/mL |
| GM-CSF | 125 µg/m$^2$ daily for 14 wks followed by 14 days rest |
| Allovectin-7 ® | 2 mg IL qwk for 6 wks |
| Afatinib | 20-50 mg daily |
| Bevacizumab | 5-15 mg/kg q14d-q21d |
| Cetuximab | 400 mg/m$^2$ followed by weekly maintenance at 250 mg/m$^2$ |
| Dasatinib | 100 mg daily |
| Erlotinib | 100-150 mg daily |
| Gefitinib | 250 mg daily |
| Imatinib | 400-600 mg daily (increased to twice daily if well tolerated or disease progresses) |
| Lapatinib | 1250 mg daily for 21 day cycle |
| Nilotinib | 400 mg twice daily |
| Panitumumab | 6 mg/kg q14d |

TABLE 1-continued

Example systemic immunomodulatory or targeted anticancer agents

| Systemic Agent | Typical Dose Schedule |
|---|---|
| Pazopanib | 800 mg daily |
| Pegaptanib | 0.3 mg q6wks |
| Ranibizumab | 0.5 mg q4wks |
| Sorafenib | 400 mg twice daily |
| Sunitinib | 50 mg daily for 4 weeks followed by 2 week recovery |
| Trastuzumab | 4 mg/kg followed by weekly maintenance at 2 mg/kg |
| Vandetanib | 200-300 mg daily |
| Vemurafenib (PLX4032) | 960 mg twice daily |
| GSK2118436 [a] | 150 mg twice daily |
| GSK1120212 [a] | 2 mg daily |
| aminoglutethimide | 250 mg q6h |
| Anastrozole | 1 mg daily |
| Exemestane | 25 mg daily |
| Fadrozole | 1 mg twice daily |
| Formestane | 250 mg daily |
| Letrozole | 2.5 mg daily |
| Vorozole | 2.5 mg daily |
| Raloxifene | 60 mg daily |
| Tamoxifen | 20-40 mg daily |
| Toremifene | 60 mg daily |
| Celecoxib | 200-400 mg twice daily |
| Rofecoxib | 20-25 mg daily |
| Suramin | 1 g qwk |
| thrombospondin (ABT-510 [a]) | 20 mg daily to 100 mg twice daily |

[a] Proprietary code name for drug under development for which no nonproprietary name is currently available.

Because of additive or synergistic effects, the combination therapies and method of treatment of the present invention will generally allow use of the systemic agent at a level at or below the typical dose schedule for the systemic agent, such as those described in Table 1, when used with a local immunomodulative therapy, such as that described infra.

Local immunomodulative therapy includes but is not limited to intralesional chemoablation using an IL chemoablative agent consisting primarily of rose bengal (4,5,6,7-tetrachloro-2',4',5',7'-tetraiodofluorescein) or another halogenated xanthene, including erythrosin B, phloxine B, 4,5,6,7-tetrabromo-2',4',5',7'-tetraiodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein in an appropriate pharmaceutical composition, including a 0.1% (w/v) or higher concentration aqueous solution of rose bengal (i.e., PV-10) or equivalent solution of another halogenated xanthene or mixtures thereof. A physiologically acceptable salt of the halogenated xanthene may be used in this composition.

The present invention includes immunotherapeutic procedures wherein large amounts of tumor antigen are exposed to a patient's immune system, for example upon intralesional delivery of an immunomodulator, including but not limited to intralesional rose bengal, in combination with one or more systemic immunomodulator, to enhance the immune-mediated antitumor response.

About the preferred IL chemoablative agents:

Local immunomodulative therapy includes, as a preferred embodiment, intralesional chemoablation using rose bengal or another halogenated xanthene. A preferred form, rose bengal disodium, has the following formula:

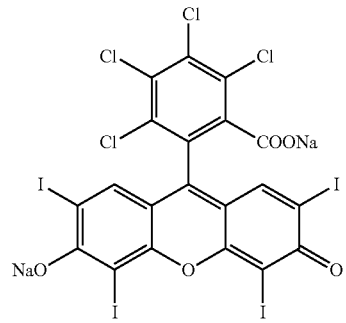

Certain details of this preferred embodiment for the local immunomodulative composition are described in Applicants' co-pending application U.S. Ser. No. 12/315,781, which is incorporated herein in its entirety. This preferred embodiment of the present invention is described here with particular relevance to melanoma. However, the present invention may also find application for the treatment of other hyperproliferative diseases including, but not limited to, cancers, such as for example, breast cancer, primary and metastatic liver cancer, prostate cancer and small cell and non small cell lung cancer, and no limitation is intended thereby.

Malignant melanoma is the most serious form of skin cancer and accounts for 80% of skin cancer deaths.

The extent of spread of a disease is described by stages. Stage 0 melanoma is a very early stage disease known as melanoma in situ. Patients with melanoma in situ are classified as Tis (tumor in situ). The tumor is limited to the epidermis with no invasion of surrounding tissues, lymph nodes, or distant sites. Melanoma in situ is considered to be very low risk for disease recurrence or spread to lymph nodes or distant sites. Treatment is by surgical excision with a margin of healthy skin.

In stage I melanoma, the tumor has penetrated in to the skin by less than 1 mm but has not spread. Treatment is by wide local excision and the probability of disease free survival in five years is between 90 to 95%.

Stage II melanoma describes a tumor that has penetrated more than 1 mm into the skin but has not spread. Wide local excision is the preferred treatment. However, excision at this stage carries a much higher risk and less favorable prognosis than excision of a Stage I tumor.

Stage III melanoma is characterized by the existence of one or more nodal, in-transit or satellite metastasis but has not spread to distant or visceral sites. In-transit metastases are distant from the primary tumor but not reaching the draining nodal basin. Satellite metastases are intralymphatic extensions of the primary tumor and are typically found closer to the primary tumor than in-transit metastasis. Five year survival for stage m patients ranges from approximately 24% (gross nodal disease) to 80% (microscopic nodal disease).

Stage IV melanoma is when the disease has spread to distant sites. Survival of stage IV melanoma drops to approximately 10%.

Similar staging systems exist for all major cancers, and are generally based on the clinical presentation and histopathologic details of the disease and how these factors have been shown to impact survival.

Standard treatment for easily removable Stage III tumors is wide area excision together with removal of lymph nodes. Adjunct treatment such as radiotherapy and chemotherapy and for regional limb metastases, regional infusion of melphalan or other chemotherapeutic agents may also be given. However, in some cases, surgery is contraindicated due to the number and/or location of tumors and other treatment options must be considered. Unfortunately, response levels for these other options are not high. For example, melanoma is largely resistant to radiation therapy. Systemic chemotherapy also has modest response rates against melanoma. The most effective chemotherapy regimen to-date is single-agent dacarbazine, which is only successful in 10-15% of cases. Two combination chemotherapy regimens commonly used in the treatment of patients with advanced-stage melanoma are the cisplatin, vinblastine and DTIC (CVD) regimen and the Dartmouth regimen, which is a combination of cisplatin, DTIC, carmustine and tamoxifen.

When melanoma occurs in the extremities, chemotherapy agents may be delivered via hyperthermic isolated limb perfusion (ILP). With this technique, blood vessels are accessed surgically, the blood flow to and from the limb is stopped using a tourniquet, and a warmed solution of chemotherapy drug is administered directly into the blood of the limb, allowing higher doses of drugs to be dispensed than with systemic treatment. A less invasive regional therapy is isolated limb infusion (ILI) whereby vascular access is gained via a percutaneous route in the groin.

Another treatment option is intralesional therapy in which a chemotherapeutic agent is injected directly into the tumor. Bacille Calmette Guerin (BCG) was one of the earliest reagents used for IL therapy. A review of data from 15 trials found 19% complete response (CR) and 26% partial response (PR) with extended survival in 13% of stage III patients.

IL interferons (IFN) have yielded mixed results ranging from a report of 45% objective response rate (ORR, 31% CR+14% PR) for IFN-α to either no result or transient response with IFN-γ. Both regimes produced significant toxicity and side effects.

IL interleukin-2 appears to be the most promising IL therapy to date with an ORR in 83% of patients (62% CR+21% PR) receiving 2-3 weekly IL treatments. Some patients reported flu like symptoms and some authors noted that although new lesions appeared during the course of treatment, some patients experienced a marked slowing of the appearance of new cutaneous lesions.

IL therapy with cisplatin or IL cisplatin with electroporation has yielded results ranging from 38% ORR (19% CR+19% PR) to 53% ORR (47% CR+7% PR). However, the ORR reported for lesions with a median diameter of 0.6 cm of 53% decreased to 44% for lesions having a median diameter of 3.0 cm.

Substantial efficacy has been reported upon a single electrochemotherapy treatment with IL bleomycin. However, as with cisplatin, response was generally reduced in larger tumors.

It may be appreciated that there remains a need for alternative methods for the treatment of hyperproliferative diseases and in particular stage m and IV melanoma.

According to a preferred embodiment of the present invention, there is provided a method for the treatment of cancer in a patient, such as metastatic melanoma, the method comprising treatment of the cancer patient with a local immunomodulative therapy combined with one or more systemic immunomodulatory therapy or systemic targeted therapy, wherein said local immunomodulatory therapy comprises intralesional administration of a chemoablative pharmaceutical composition comprising a hydrophilic vehicle containing 4,5,6,7-Tetrachloro-2',4',5',7'-tetraiodofluorescein (i.e. rose bengal), or certain other halogenated xanthene, or a physiologically acceptable salt thereof. It is preferred that the halogenated xanthene be present in this pharmaceutical composition at a concentration of about 0.1% (w/v) up to about 20% (w/v), and that the pharmaceutical composition include an electrolyte comprising at least one cation selected from the group consisting of sodium, potassium, calcium and magnesium and at least one anion selected from the group consisting of chloride, phosphate and nitrate, wherein the electrolyte is at a concentration of between about 0.1% (w/v) and about 2% (w/v). It is also preferred that the pH of the pharmaceutical composition be between about 4 to about 10.

The term "physiologically acceptable salt" refers to any non-toxic alkali metal, alkaline earth metal, and ammonium salt commonly used in the pharmaceutical industry, including the sodium, potassium, lithium, calcium, magnesium, barium, ammonium and protamine zinc salts, which can be prepared by methods known in the art. Preferably, the salts are sodium, potassium, calcium and ammonium in either the mono or dibasic salt form.

Especially preferred in this IL chemoablative pharmaceutical composition is the disodium salt of rose bengal. Previous work by one or more of the present inventors (WO 02/05812) reported their discovery that rose bengal exhibits preferential uptake into cancer cells but is essentially excluded from normal cells.

One or more of the present inventors have also reported their discovery that the nature of the vehicle in which the halogenated xanthene, or a physiologically acceptable salt thereof, is administered can significantly influence the degree of partitioning into tumor cells. In particular, one or more of the present inventors have surprisingly discovered that at an electrolyte concentration of between about 0.1% (w/v) and about 2.0% (w/v), partitioning into tumor cells may rapidly be increased.

An approximation of an agent's potential for tissue accumulation can be estimated based upon the partition coefficient $K_p$. This in vitro parameter is purported to have predictive values relating to in vitro delivery at the cellular level. In particular, a value greater than unity is considered to indicate agents capable of localizing in tissue, and thereby being capable of exhibiting enhanced chemotherapeutic efficacy in such tissue. One or more of the present inventors surmise that values much greater than approximately 50-100 may indicate excess lipophilicity (tendency to accumulate in organic environments) that may compromise delivery of an agent in a desirable aqueous (i.e., hydrophilic) formulation. $K_p$ is determined by measuring the ratio of equilibrium concentrations of an agent in a lipophilic phase (n-octanol) contacted with an aqueous phase.

One or more of the present inventors have also reported their discovery that it is preferred that the pH of the IL chemoablative pharmaceutical composition is in the range of between about 4 to about 10, and more preferably between about 5 to about 9, to yield maximum solubility of the halogenated xanthene in an aqueous vehicle and assure compatibility with biological tissue. A particularly preferred pH is between about 4 to about 7, preferably between about 5 to about 7, more preferably between about 6 to about 7. At these pH values, the halogenated xanthenes generally remain in dibasic form, rather than the water insoluble lactone that forms at low pH.

The pH of the IL chemoablative pharmaceutical composition may be regulated or adjusted by any suitable means known to those of skill in the art. The composition may be buffered or the pH adjusted by addition of acid or base or the like. As the halogenated xanthenes, or physiologically acceptable salts thereof, are weak acids, depending upon halogenated xanthene concentration and/or electrolyte concentration, the pH of the composition may not require the use of a buffer and/or pH modifying agent. It is especially preferred, however, that the composition does not contain any buffer, allowing it to conform to the biological environment once administered.

One or more of the present inventors have also reported their discovery that $K_p$ is also dependent upon electrolyte concentration with the $K_p$ value increasing with electrolyte concentration. Particularly preferred concentrations of electrolyte in the IL chemoablative pharmaceutical composition are between 0.5 to 1.5% (w/v), and even more preferably at a concentration of about 0.8 to 1.2% (w/v) and most preferably at a concentration of about 0.9% (w/v), this latter concentration being especially preferred since it corresponds to an approximately isotonic solution.

In a further preferred embodiment of the present invention, the electrolyte in the IL chemoablative pharmaceutical composition is sodium chloride.

Electrolytes at such levels increase the osmolality of the IL chemoablative pharmaceutical composition. Thus, as an alternative to specifying a range of electrolyte concentrations, osmolality may be used to characterize, in part, the electrolyte level of the composition. It is preferred that the osmolality of the composition be greater than about 100 mOsm/kg, and more preferably that the osmolality of the composition be greater than about 250 mOsm/kg and most preferably that it is about 300-500 mOsm/kg.

One or more of the present inventors have found that the preferred concentration of halogenated xanthene and/or dose of IL chemoablative pharmaceutical composition will be dependent upon factors including, but not limited to, tumor size, number and location. For visceral or other internal lesions, such as cancers of the liver, intralesional administration may be by percutaneous or intraoperative administration.

One or more of the present inventors have also found that halogenated xanthene concentrations in the IL chemoablative pharmaceutical composition above about 1% (w/v) to 3% (w/v) are particularly useful for chemoablative use, since lower concentrations are generally insufficient to directly elicit destruction of target tissues. Thus, in a preferred embodiment, the concentration of halogenated xanthene is in the range of from about 3% (w/v) to about 20% (w/v). In another embodiment, the concentration of halogenated xanthene is from about 3% (w/v) to about 10% (w/v). In another embodiment, the concentration of halogenated xanthene is from about 10% (w/v) to about 20% (w/v). In still another embodiment, the concentration of halogenated xanthene is about 10% (w/v). One or more of the present inventors have surprisingly found that at these concentrations, not only can an efficient therapeutic response be obtained, but the solution is also highly stable and can be readily handled both in manufacture and use. These preferred concentrations may be expressed in weight to volume (w/v), however, concentration in weight to weight (w/w) is substantially equivalent.

Typical dosages of the IL chemoablative pharmaceutical composition administered by IL administration range from between 0.1 mL/cc lesion volume to about 2 mL/cc lesion volume, most preferably between about 0.25 mL/cc to about 0.75 mL/cc lesion volume. Such doses typically correspond to a patient dose of between about 10 mg to about 1500 mg of halogenated xanthene (which are significantly higher than those doses used for diagnostic liver tests).

Since the pharmaceutical composition is for IL administration, which is an intracorporeal route, it is further preferred that it be sterile, such as required for conformance to U. S. Pharmacopeia (USP) test <71>, and further that it contains negligible levels of pyrogenic material, such that it conforms to USP<85> (limulus amebocyte lysate assay) or to USP <151> (rabbit pyrogen test), or to substantially equivalent requirements, at a pyrogen or endotoxin level equivalent to not more that (NMT) 10 endotoxin units (EU) per mL. Moreover, the pharmaceutical composition should conform to requirements limiting content of particulate matter as defined in USP <788> (i.e., NMT 3000 particulates greater than 10 microns in size, and NMT 300 particulates greater than 25 microns in size, per container) or substantially equivalent requirements. Each of these references from the USP is incorporated herein by reference.

Still further, one or more of the present inventors have found that a hydrophilic vehicle is preferred for the pharmaceutical composition to maximize preference of the halogenated xanthene for partitioning into cancerous tissue. Accordingly, it is preferred that the pharmaceutical composition contains a minimum of non-hydrophilic components that might interfere with such partitioning. It is preferred that the hydrophilic vehicle is water, and it is most preferred that this pharmaceutical composition consists substantially of water.

One or more of the present inventors have found that such pharmaceutical compositions as described herein are optimally packaged in glass vials having a capacity of approximately 1 to 10 mL, and more preferably approximately 5 mL. Such capacities are well suited as unidose forms (i.e., single use packages) for IL treatments.

In a preferred embodiment, the formulation of the pharmaceutical composition is not buffered. In this case, it is preferred that packaging containers be made of the USP Type I (low extractable or chemically resistant borosiciliate) or USP Type II (low-extractable soda lime) glass and that the inside surface of such glass containers be surface treated to reduce surface alkalinity of the container that could adversely affect pH or long-term stability. Typical surface treatment applicable to such containers is described in USP<661>. The inside of such surface-treated glass containers should be rinsed with a suitable solvent, such as distilled water one or more times prior to filling in order to remove any residue of such surface treatment. The containers should also be depyrogenated prior to filling, for example, by heating to 250° C. or higher for several hours or more, and should be sterile or sterilized prior to filling using methods common in the field. If is further preferred that such containers have a minimum neck size, for example, of less than 10 mm and more preferably 5 mm or less, to reduce surface area of the closures of the containers (and hence exposure of the medicament to such closures).

One or more of the present inventors have further found that a septum-type closure, composed preferably of a pharmaceutical grade elastomeric material with a Teflon or similar inner coating, is particularly suitable for use with the IL chemoablative pharmaceutical composition since it facilitates insertion of a needle into the container for withdrawal of a dose of medicament while exhibiting minimal potential for interaction with the container contents.

It is also preferred that the pharmaceutical composition does not include any preservatives. One or more of the present inventors have found that it is generally preferable to avoid use of preservatives, many of which may deleteriously interfere with the pharmaceutical composition or formulation thereof, or may complex or otherwise interact with or interfere with the delivery of the halogenated xanthene active component. To the extent that a preservative may be used, one or more of the present inventors have found that imidurea is preferred as it does not interact with halogenated xanthenes, either in the pharmaceutical composition or upon administration.

This description has been offered for illustrative purposes only and is not intended to limit the invention of this application.

What is claimed as new and desired to be protected by Letters Patent is set forth in the appended claims.

The invention claimed is:

1. A method of treatment of a solid tumor cancer in a human comprising separately administering a therapeutically effective amount of: (1) an intralesional chemoablative pharmaceutical composition to elicit ablation of at least one cancerous tumor; and (2) a therapeutically effective amount of a systemic immunomodulatory anticancer agent that is a systemic inhibitor of immune system down-regulation or that is a systemic enhancer of immune system up-regulation in a combination therapeutic regime,
wherein said intralesional chemoablative pharmaceutical composition comprises an intralesional (IL) chemoablative agent comprising rose bengal (4,5,6,7-tetrachloro-2',4',5',7'-tetraiodofluorescein) in an appropriate pharmaceutical composition, including a 0.1% (w/v) up to about 20% (w/v) aqueous solution of rose bengal, or a physiologically acceptable salt of rose bengal, said intralesional chemoablative pharmaceutical composition being administered intralesionally into said at least one cancerous tumor at about 0.1 mL/cc lesion volume to about 2 mL/cc lesion volume.

2. The method of claim 1, wherein the rose bengal salt is rose bengal disodium.

3. The method of claim 1, wherein said pharmaceutical composition includes an electrolyte comprising at least one cation selected from the group consisting of sodium, potassium, calcium and magnesium and at least one anion selected from the group consisting of chloride, phosphate and nitrate, wherein the electrolyte is at a concentration of between about 0.1% (w/v) and about 2% (w/v).

4. The method of claim 3, wherein the concentration of said electrolyte in the IL chemoablative pharmaceutical composition is between 0.5 to 1.5% (w/v).

5. The method of claim 1, wherein said chemoablative pharmaceutical composition has an osmolality of the composition of greater than about 100 mOsm/kg.

6. The method of claim 3, wherein said electrolyte is sodium chloride.

7. The method of claim 1, wherein said intralesional chemoablative pharmaceutical composition comprises a hydrophilic vehicle.

8. The method of claim 1, wherein said pharmaceutical composition has a pH in the range of between about 4 to about 10.

9. The method of claim 8, wherein said pharmaceutical composition has a pH in the range of between about 5 to about 7.

10. The method of claim 1, wherein said administration of said systemic immunomodulatory anticancer agent is commenced prior to administration of said intralesional chemoablative pharmaceutical composition.

11. A method of treatment of a solid tumor cancer in a human comprising administering a therapeutically effective amount of: (1) an intralesional chemoablative pharmaceutical composition to elicit ablation of at least one cancerous tumor; and (2) a therapeutically effective amount of a systemic immunomodulatory anticancer agent that is a systemic inhibitor of immune system down-regulation comprising anti-CTLA-4 antibodies, anti-PD-L1 antibodies, or anti-PD-1 antibodies, in a combination therapeutic regimen,
wherein said intralesional chemoablative pharmaceutical composition comprises an intralesional (IL) chemoablative agent comprising rose bengal (4,5,6,7-tetrachloro-2',4',5',7'-tetraiodofluorescein) in an appropriate pharmaceutical composition, including a 0.1% (w/v) up to about 20% (w/v) aqueous solution of rose bengal, or a physiologically acceptable salt of rose bengal, said intralesional chemoablative pharmaceutical composition being administered intralesionally into said at least one cancerous tumor at about 0.1 mL/cc lesion volume to about 2 mL/cc lesion volume.

12. A method of treatment of a solid tumor cancer in a human comprising separately administering a therapeutically effective amount of: (1) an intralesional chemoablative pharmaceutical composition to elicit ablation of at least one cancerous tumor; and (2) a therapeutically effective amount of a systemic immunomodulatory anticancer agent that comprises anti-CTLA-4 antibodies, anti-PD-L1 antibodies, or anti-PD-1 antibodies, wherein said intralesional chemoablative pharmaceutical composition comprises an intralesional (IL) chemoablative agent comprising a halogenated xanthene in an appropriate pharmaceutical composition, including a 0.1% (w/v) up to about 20% (w/v) aqueous solution of the halogenated xanthene or mixtures thereof, or a physiologically acceptable salt of the halogenated xanthene.

13. The method of claim 12, wherein the halogenated xanthene is selected from the group consisting of erythrosin B, phloxine B, 4,5,6,7-tetrabromo-2',4',5',7'-tetraiodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'- triiodofluorescein, 4,5,6,7-tetrabromo-2',4',5'-triiodofluorescein, and 4,5,6,7-tetrabromo-2',4',7'-triiodofluorescein.

14. The method of claim 12, wherein the halogenated xanthene is rose bengal (4,5,6,7-tetrachloro-2',4',5',7'-tetraiodofluorescein) or a physiologically acceptable salt of rose bengal.

15. The method of claim 14 wherein the halogenated xanthene is rose bengal disodium.

16. The method of claim 13, wherein said rose bengal is present at a concentration of about 0.1% (w/v) up to about 20% (w/v), and the pharmaceutical composition includes an electrolyte comprising at least one cation selected from the group consisting of sodium, potassium, calcium and magnesium and at least one anion selected from the group consisting of chloride, phosphate and nitrate, wherein the electrolyte is at a concentration of between about 0.1% (w/v) and about 2% (w/v).

17. The method of claim 16, wherein the concentration of said electrolyte in the IL chemoablative pharmaceutical composition is between 0.5 to 1.5% (w/v).

18. The method of claim 17, wherein said chemoablative pharmaceutical composition has an osmolality of the composition of greater than about 100 mOsm/kg.

19. The method of claim 16, wherein said electrolyte is sodium chloride.

20. The method of claim 13, wherein said pharmaceutical composition comprises a hydrophilic vehicle.

21. The method of claim 13, wherein said pharmaceutical composition has a pH value in the range of about 4 to about 10.

22. The method of claim 21, wherein said pharmaceutical composition has a pH value in the range of about 5 to about 7.

23. The method of claim 1, wherein said systemic immunomodulatory anticancer agent comprises anti-CTLA-4 antibodies, anti-PD-L1 antibodies, or anti-PD-1 antibodies.

24. The method of claim 1, wherein said tumor is selected from the group consisting of melanoma, breast cancer, primary and metastatic liver cancer, prostate cancer and small cell and non small cell lung cancer.

25. The method of claim 11, wherein said tumor is selected from the group consisting of melanoma, breast cancer, primary and metastatic liver cancer, prostate cancer and small cell and non small cell lung cancer.

26. The method of claim 12, wherein said tumor is selected from the group consisting of melanoma, breast cancer, primary and metastatic liver cancer, prostate cancer and small cell and non small cell lung cancer.

* * * * *